United States Patent
Denholm (10) Patent No.: US 7,263,669 B2
(45) Date of Patent: Aug. 28, 2007

(54) PATIENT COMMUNICATION METHOD AND SYSTEM

(75) Inventor: Diana B. Denholm, West Palm Beach, FL (US)

(73) Assignee: Denholm Enterprises, Inc., West Palm Beach, FL (US)

(*) Notice: Subject to any disclaimer, the term of this patent is extended or adjusted under 35 U.S.C. 154(b) by 820 days.

(21) Appl. No.: 10/291,163

(22) Filed: Nov. 8, 2002

(65) Prior Publication Data

US 2003/0093300 A1 May 15, 2003

Related U.S. Application Data

(60) Provisional application No. 60/332,819, filed on Nov. 14, 2001.

(51) Int. Cl.
*G06F 3/00* (2006.01)

(52) U.S. Cl. .................. 715/827; 725/78; 340/286.07; 434/112

(58) Field of Classification Search ................. 715/827; 725/78; 340/286.07; 434/112
See application file for complete search history.

(56) References Cited

U.S. PATENT DOCUMENTS

| | | | |
|---|---|---|---|
| 4,465,465 A | 8/1984 | Nelson | 434/112 |
| 4,642,610 A | 2/1987 | Smith, III | 340/365 S |
| 4,761,633 A * | 8/1988 | Leff et al. | 340/286.07 |
| 4,916,435 A | 4/1990 | Fuller | |
| 5,051,924 A | 9/1991 | Bergeron et al. | 364/513.5 |
| 5,086,391 A * | 2/1992 | Chambers | 340/573.1 |
| 5,097,469 A * | 3/1992 | Douglas | 714/712 |
| 5,299,125 A | 3/1994 | Baker et al. | 364/419.08 |
| 5,317,671 A | 5/1994 | Baker et al. | 395/2 |
| 5,384,701 A * | 1/1995 | Stentiford et al. | 704/3 |
| 5,444,768 A | 8/1995 | Lemaire et al. | 379/68 |
| 5,588,839 A | 12/1996 | Shimoda | 434/114 |
| 5,600,311 A * | 2/1997 | Rice et al. | 340/825.19 |
| 5,657,380 A * | 8/1997 | Mozer | 379/88.01 |
| 5,822,544 A | 10/1998 | Chaco et al. | 395/202 |
| 5,867,821 A * | 2/1999 | Ballantyne et al. | 705/2 |
| 5,899,855 A | 5/1999 | Brown | |
| 5,901,246 A | 5/1999 | Hoffberg et al. | 382/209 |
| 5,950,632 A * | 9/1999 | Reber et al. | 128/898 |
| 5,974,262 A | 10/1999 | Fuller et al. | 395/838 |
| 6,014,689 A * | 1/2000 | Budge et al. | 709/206 |
| 6,246,573 B1 * | 6/2001 | Khan et al. | 361/683 |
| 6,249,809 B1 | 6/2001 | Bro | 709/217 |

(Continued)

OTHER PUBLICATIONS

Couter, Gini and Annette Marquis, Mastering Microsoft Office 2000 Professional Edition, 1999, Sybex, Professional Edition, pp. 14-18 and 166-168.*

*Primary Examiner*—Kristine Kincaid
*Assistant Examiner*—Ryan F. Pitaro
(74) *Attorney, Agent, or Firm*—Akerman Senterfitt (57) ABSTRACT

A healthcare communication system can include a patient terminal having a keyboard unit with message keys for transmitting different ones of one or more programmed messages, and alphanumeric keys for composing messages. The patient terminal can be communicatively linked to a patient terminal display for presenting the programmed messages and composed messages. Each of the message keys can include identifying indicia associated with a programmed message transmitted upon selection of the message key. The patient terminal keyboard also can include one or more destination keys for specifying one of multiple destination addresses within the healthcare communication system for delivering individual ones of the messages.

23 Claims, 7 Drawing Sheets

U.S. PATENT DOCUMENTS

| | | |
|---|---|---|
| 6,304,848 B1 | 10/2001 | Singer |
| 6,377,162 B1* | 4/2002 | Delestienne et al. ... 340/286.07 |
| 6,394,356 B1* | 5/2002 | Zagami ...................... 235/487 |
| 6,409,662 B1 | 6/2002 | Lloyd et al. |
| 6,421,707 B1* | 7/2002 | Miller et al. ................ 709/206 |
| 6,553,106 B1 | 4/2003 | Gould et al. |
| 2002/0196141 A1* | 12/2002 | Boone et al. ................ 340/540 |
| 2003/0062989 A1* | 4/2003 | Tsunezumi ............. 340/286.07 |
| 2004/0015132 A1* | 1/2004 | Brown ........................ 604/131 |

\* cited by examiner

Room number: 367-A

Phone number: 555-123

Today is Wednesday, August 8, 2001

The time is 9:57 a.m.

Nurse on Duty:

John Smith, R.N.

Room temperature: 75

Outside temperature: 92

Patient: Sue, did you remember to water my orchids?

Visitor Center: Yes, I did. Is there anything else you need?

Patient: Yes, please tell everyone I am doing fine.

Room number: 367-A

Phone number: 555-123

Today is Wednesday, August 8, 2001

The time is 9:57 a.m.

Nurse on Duty:

John Smith, R.N.

Room temperature: 75

Outside temperature: 92

Room number: 367-A

Phone number: 555-123

Today is Wednesday, August 8, 2001

The time is 9:57 a.m.

Nurse on Duty:

John Smith, R.N.

Room temperature: 75

Outside temperature: 92

Hello Mary Smith,
    The nutrition staff would like to offer you the following choices for lunch today.

Main Course:
1. Peanut butter sandwich
2. Egg salad sandwich
3. Sliced turkey

Please enter the number for your choices on the keypad. Your lunch will be delivered around 12:10.

Room number: 367-A

Phone number: 555-123

Today is Wednesday, August 8, 2001

The time is 9:57 a.m.

Nurse on Duty:

John Smith, R.N.

Room temperature: 75

Outside temperature: 92

Hello Mary Smith,
   Your light for needing to go to the bathroom is on.
Do you need me to come right back? If not, just press your cancel button.
         John Smith, R.N.

FIGURE 8

PATIENT COMMUNICATION METHOD AND SYSTEM

CROSS-REFERENCE TO RELATED APPLICATIONS

This application claims the benefit of U.S. Provisional Patent Application No. 60/332,819, filed in the United States Patent and Trademark Office on Nov. 14, 2001.

BACKGROUND OF THE INVENTION

1. Technical Field

This invention relates to the medical field, and more particularly, to facilitating communications between a patient, care-givers, visitors, and the like.

2. Description of the Related Art

Oftentimes, patients are unable, or have difficulty, speaking with care-givers, visitors, and other personnel. This inability to speak clearly can make communications between the patient and others difficult. Typically, patients experience such speaking difficulties as a result of a particular medical treatment. Such is the case when a patient must be intubated or when the patient requires an inter-tracheal tube. Patients also can experience difficulty speaking, not as the result of a medical treatment, but as a direct result of an ailment, infirmity, or other medical condition. In any case, many situations arise in which a patient experiences either a loss of the ability to speak or difficulties in speaking.

Presently, when a patient who is unable to verbally communicate needs to communicate with care-givers, the patient uses a call button to effectively page personnel. As a normal intercom response from a nurse cannot verbally be answered by the patient, this generally requires that the nurse come to the room to find out what the patient needs. In consequence, the nurse must visit the patient. This can result in additional work for the nurse as a second, and even third trip, may be necessary, but cannot be determined until after the nurse has visited with the patient.

Alternative communication methods can be used in the case where a patient who is unable to verbally communicate wants to communicate with other persons within the same room. The patient can be given a sheet of paper having printed thereon the letters of the alphabet. The patient is asked to point to the letters one by one in order to spell words. This speech alternative, however, does have disadvantages. For example, detecting where one word ends and another word begins can be difficult. Consequently, as the patient points to the letters, the person with whom he is trying to communicate may not be able to follow what the patient is trying to articulate. Further adding to the problem, the patient may lack manual dexterity as a result of a medical treatment or condition and have difficulty pointing to desired letters. In an emergency, this can create a life-threatening situation.

Handwritten notes can provide another alternative to verbal communication. Some of the disadvantages associated with the use of a letter chart, however, also can apply to the use of handwritten notes. In fact, handwritten communications can require more manual dexterity than merely pointing to a letter and, at best, are tediously slow. Another disadvantage is that passing notes amidst the large number of cables, wires, monitors, tubes, and other medical equipment often proves difficult. Moreover, while fumbling for pen and paper or passing a note, one can inadvertently disconnect a monitor or tube thereby endangering the patient.

Conventional healthcare monitoring equipment, for example of the variety often used within intensive care units, is often thought to preclude the need for patients to call a nurse. Such equipment, however, can generate erroneous alerts and/or signals, must be reset from time to time, and may not be able to respond to each emergency need of a patient. Still, patients can have other needs or reasons for calling a nurse other than those which are monitored by conventional monitoring equipment.

While some attempts have been made to develop more effective patient communication systems, such systems have yet to adequately address the needs of patients lacking the ability to communicate verbally. Moreover, many systems do not facilitate communications between the patient and other persons in the same room, various hospital service personnel, or with visitors in remote locations whether or not they have the ability to speak.

BRIEF DESCRIPTION OF THE DRAWINGS

There are shown in the drawings embodiments which are presently preferred, it being understood, however, that the invention is not limited to the precise arrangements and instrumentalities shown.

SUMMARY OF THE INVENTION

The invention disclosed herein provides a method and system for facilitating communications between a patient, care-givers, and visitors in cases where the patient may be unable or unwilling to speak. The present invention enables patients to communicate with care-givers located throughout a care-taking facility, such as a hospital, assisted living facility, and the like. Using the invention, patients also can communicate with visitors who are located at a visitor center which is remotely located from the patient's room, as well as visitors in the immediate vicinity. Data relating to the administration and delivery of different care-giver services, including but not limited to, response times to patient requests, can be logged and tracked.

One aspect of the present invention can include a healthcare communication system. The system can include a patient terminal having a keyboard unit having message keys for transmitting different ones of one or more programmed messages. The keyboard also can include alphanumeric keys for composing messages. The patient terminal can be communicatively linked to a patient terminal display for presenting the programmed messages and composed messages. Each of the message keys can include identifying indicia associated with a programmed message transmitted after selection of the message key. The patient terminal keyboard also can include one or more destination keys for specifying one of multiple destination addresses within the healthcare communication system for delivering individual ones of the messages.

The patient terminal display can be configured to display an image of at least one care-giver assigned to a user of the patient terminal. The patient terminal display can be disposed within the patient terminal. Additionally, the patient terminal can include a wireless communication component for transmitting the messages to at least one receiving station. Notably, the messages can be text messages, audio messages, visual messages, and/or audiovisual messages. According to one embodiment of the present invention, a first activation of one of the message keys can cause a notification to be provided which indicates the identity of the activated message key. A second activation of the message key can cause a message associated with the activated message key to be sent.

The system further can include a visitor station communicatively linked to the patient terminal. The visitor station can include an audiovisual component for generating audiovisual information of at least one visitor and playing received audiovisual information. The patient terminal can include an audiovisual component for generating audiovisual information and for playing the audiovisual information from the visitor station. A data store can be included in the system for recording the audiovisual data for delayed playback through the visitor station or the patient terminal.

For example, the visual information of the audiovisual information generated by the patient terminal can specify an image of a user of the patient terminal. Accordingly, the visitor station can be configured to display the image of the user. Similarly, the visual information of the audiovisual information generated by the visitor station can specify an image of a visitor using the visitor station. As the visual information can be presented through the patient terminal display, the patient terminal display can be configured to display the image of the visitor.

The healthcare communication system can include a second display having one or more visual status indicators corresponding to the programmed messages, wherein one of the visual status indicators is illuminated responsive to a user selection of a corresponding one of the programmed messages. The system further can include a nutrition station configured to transmit messages specifying one or more food item choices to the patient terminal for presentation upon the patient terminal display. The nutrition station also can receive messages from the patient terminal specifying selected ones of the food item choices indicating food items to be prepared and delivered. Accordingly, the data store further can include patient specific dietary information. The nutrition station can be configured to present only those food item choices which conform to the patient specific dietary information.

The healthcare communication system also can include a nursing station. The nursing station can include a keyboard and display. The nursing station can be configured to receive the messages and to transmit messages to the patient terminal. According to one embodiment of the nursing station, the terminal of the nursing station can be configured to display a listing of one or more authorized visitors, unauthorized visitors, or both authorized and unauthorized visitors for particular patients. In addition to the listing of visitors, visual images of the authorized and/or unauthorized visitors can be displayed such that nursing staff can recognize such persons by sight.

A message logger can be included in the healthcare communication system. The message logger can store, within the data store, message transmission information and message response information for messages generated by the patient terminal, the nutrition station, and the nursing station. The system further can include an administrative station configured to generate performance metric reports according to the message transmission information and the message response information.

The patient communication system can include a translation system which is configured to translate text specified in various messages exchanged among the stations disclosed herein from a first language to a second language. A speech recognition system can be included which can convert an audio message to text. Notably, the speech recognition system can be configured to convert an audio message to text and to provide the speech recognized text to the translation system for translation into a different language.

Another aspect of the present invention can include a method of determining the effectiveness of healthcare for use within a care-taking facility having a healthcare communication system including one or more communicatively linked healthcare stations. The method can include logging, within an electronic data store, message transmission information specifying a transmission date and time of messages initiated by a patient terminal and identifiers indicating the healthcare stations receiving the messages. Within the data store, message response information specifying a transmission date and time of messages generated by the receiving healthcare stations in response to the patient terminal initiated messages can be logged. The message transmission information and message response information can be compared to determine performance metrics for the healthcare stations. Accordingly a report can be generated specifying the performance metrics. Notably, each healthcare station can be associated with a department of the care-taking facility, and the report can be categorized according to the care-taking facility departments.

DESCRIPTION OF THE INVENTION

The invention disclosed herein provides a method and system for facilitating communications between a patient, care-givers, and visitors in cases where the patient may be unable or unwilling to speak. In particular, the invention can facilitate communications between a patient and one or more visitors within the patient's room. Additionally, using the invention, patients can communicate with visitors who are located at a visitor center which is remotely located from the patient's room. The present invention enables patients to communicate with care-givers located throughout a care-taking facility, such as a hospital, assisted living facility, and the like. Data relating to the administration and delivery of different care-giver services, including but not limited to, response times to patient requests, can be logged and tracked. Accordingly, the invention can provide various reporting functions detailing the quality of service provided by the care-taking facility and staff. The present invention can be used within any of a variety of care-giving facilities such as hospitals, nursing homes, assisted living facilities. Particular aspects of the present invention can be used within the home as well.

The present invention can facilitate communications between patients, caregivers, and visitors. The communications can be typed text messages, preprogrammed text messages, pre-programmed visual messages including visual identifiers such as icons, colors, symbols, or other alphanumeric characters corresponding to requests, responses, or services, as well as audio and/or video, whether such communications are real-time, near real-time, or are pre-recorded and stored for later use. The present invention further can provide a system for tracking the delivery of various patient care services from a quality control perspective. Still, the invention can increase the efficiency of patient service delivery.

Figure 1:
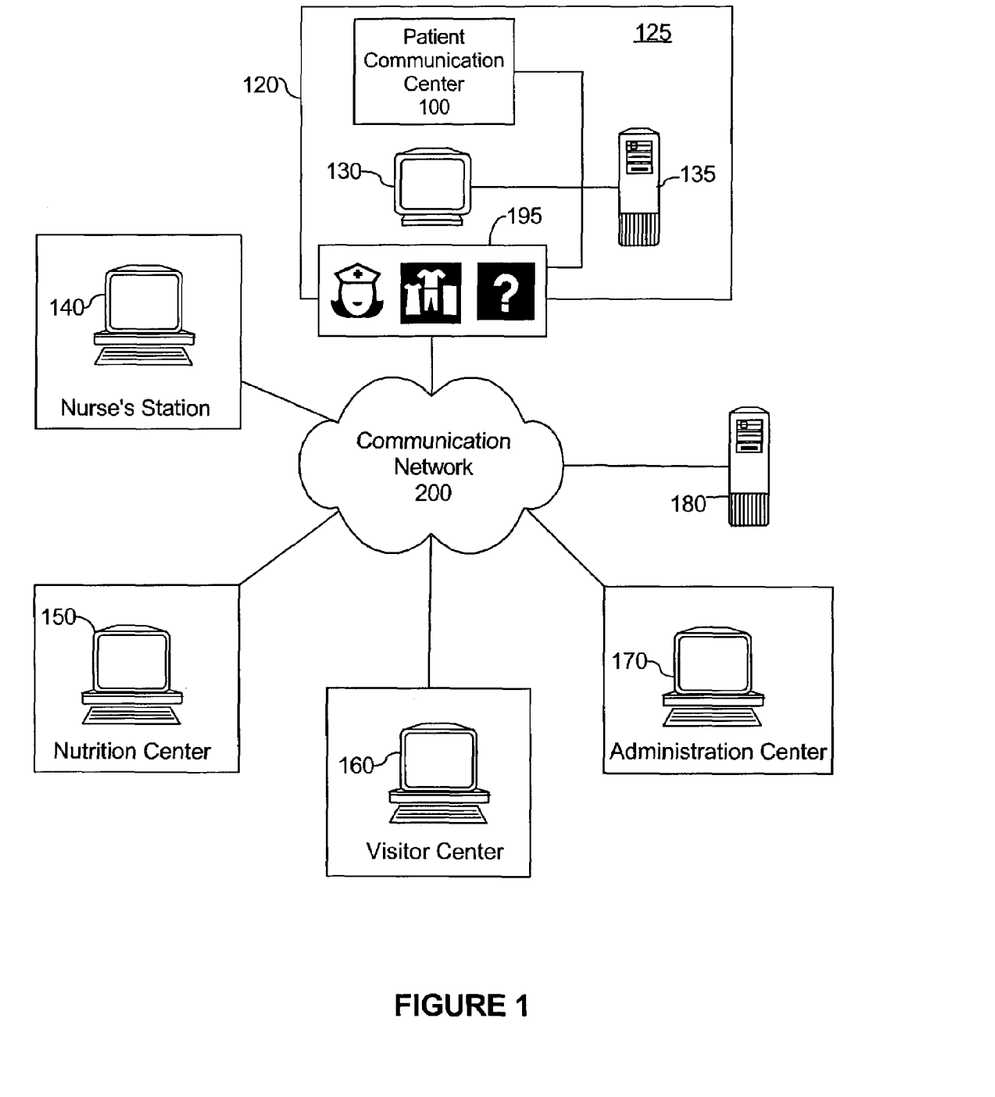
FIG. 1 is a schematic diagram illustrating a system configured in accordance with one aspect of the present invention.

FIG. 1 is a schematic diagram illustrating an exemplary patient communication system in accordance with the inventive arrangements. The patient communication system can be used to communicatively link several remote locations within a patient care center such as a hospital or other medical facility. As shown in FIG. 1, several computer systems, including a patient system 125, a nurse station computer system 140, a nutrition center computer system 150, a visitor center computer system 160, as well as hospital administration computer system 170, can be communicatively linked through the computer communications network 200. Still, other locations within a given care-taking facility can be communicatively linked if necessary and if suitably equipped.

A patient room 120 can include a patient system 125 having a patient communication center (PCC) 100, a video display 130, a patient computer 135, and a patient door display 195, each of which can be operatively connected. The PCC 100 can be a keyboard data entry module configured so that a patient can type or activate particular buttons on the PCC 100. The video display 130 can be a television, a computer monitor belonging to the computer system within the patient room 120, or another display such as a flat panel display, a liquid crystal display, or any other display suitable for displaying text and/or images. Moreover, the patient system 125 can include various peripherals such as a microphone, a camera, and headphones or speakers to facilitate communications with other similarly equipped computers connected to the computer communications network 200. Notably, the aforementioned peripherals can be located in close proximity to the patient. In one embodiment of the present invention, the microphone, speakers, and camera can be disposed within the PCC 100. Still, these components can be individual components or can be included within the video display depending upon the physical dimensions and layout of the patient room 120.

The patient door display 195 can be a video monitor, a lighted sign, or another visual display capable of displaying images. The patient door display 195 can be located inside and/or outside of the patient's room 120. For example, the patient door display 195 can be placed above, on, or to either side of the door to patient room 120. Regardless, the patient door display 195 can be configured to display particular icons responsive to activation of a corresponding button on the PCC 100. The primary function of the patient door display is to provide notice to care-giver personnel that the patient has requested a particular service. Once the service has been attended to, the icon displayed or illuminated on the patient door display 195 can be turned off.

Care-giver personnel can send and receive messages through computer system 140 at the nurse station. Accordingly, care-giver personnel can respond to patient requests and provide the patient with feedback. Notably, each of the computer systems 140-170 of FIG. 1 can be standalone computer systems having an information processing capability as well as audio visual equipment such as speakers, headsets, microphones, and cameras.

Nutrition center personnel can interact with other personnel as well as the patient through the nutrition center computer system 150 as shown. For example, through the patient communication system, the nutrition center staff can be provided with information indicating the patient's name, room number, and any foods preferred or recommended by the patient or care-giver. Any other specific dietary requirements of the patient can be entered into the a database or other data store at the time of check-in. This information can be updated as required. For example, upon check-in or during treatment, information such as whether the patient is on a low sodium or low carbohydrate diet, whether the patient is a vegetarian, and the like, can be determined. This information can be provided in text form or can be indicated through one or more visual identifiers such as color codes, alphanumeric codes, pictures, or icons.

From the nutrition center computer system 150, care-giver personnel can provide the patient with menu information. This information can be filtered, and thereby individualized, according to the patient's particular dietary requirements. The patient can make electronic menu selections which can be transmitted to the nutrition center computer system 150. Upon delivery of the food to the patient, a print-out of the patient's food selections can be provided. Notably, a record of ordered food, time stamp information corresponding to the time of order and delivery can be stored for purposes of billing and tracking nutrition center performance. The data further can be used in connection with existing inventory systems to determine when new food should be ordered, that food has expired, or to determine pricing of products.

Visitors can interact with the patient through the visitor center computer 160 as shown without having to be in the patient's room. Using the audio visual equipment of the visitor computer system 160, a patient receives realtime or near-realtime audio and/or video from the visitor center. Still, if the patient is unavailable, visitors can record audio and visual messages for a patient which can be recalled for listening and viewing at a later time. For example, if the patient is sleeping or experiencing a particularly difficult day, the patient can view or listen to the messages at a more suitable time.

Although some patients are not allowed to have visitors, or the visitors are limited to only immediate family members, the presence of certain people can stimulate recovery of the patient and provide emotional support to the visitors. Consequently, interactions through the visitor center can provide more meaningful communications to the patient simply because the patient knows that the visitor is close. The visitor center also accommodates visitors having a need to be close to the patient.

In any case, although the patient can view a visitor from the visitor center, the patient can choose whether to activate the camera within the patient's own room. In addition, the patient can specify one or more lists of allowable visitors in addition to the parameters of each visit. For example, a patient may be willing to participate in a live video visit with visitor A, but not an in-person visit. Similarly, if the patient does not want any visitors, the patient can request that any visitors must record a message which the patient can view or listen to at a later time.

The administration center computer system 170 can be used to access information, including, but not limited to patient requests, responses from care-giver personnel, as well as the identity of responding staff and the responsible or "on-duty" staff member. Such identification is intended not only for efficiency and comfort for the patient, but also as a protection for patient and nursing staff against possible violent attacks. Notably, personal communications between patients and visitors, whether in the room or the visitor station cannot be accessed by care-giver personnel through the administrative computer system 170. This information can be time and date stamped so that the information can be stored and tracked for quality assurance or other administrative purposes. For example, the administrative center computer system 170 can generate reports indicating the timeliness of responses to patient requests.

Computer system 180 can include one or more servers having one or more data stores disposed therein, for example a network server for data storage and retrieval or an application server. As previously mentioned, data can be cataloged according to the particular recipient, sender, time, date, message type, or content. For example, communications exchanged between the various stations and/or centers can be stored and time-stamped for tracking and quality control purposes. As used herein, the term "data store" can include one or more individual data stores which can be communicatively linked and/or distributed across a computer communications network.

The computer system 180 can be used to provide speech recognition and text-to-speech processing capabilities, can store recorded audio prompts, as well as other multi-media information such as audio and video as previously mentioned including messages from the visitor center. In one embodiment of the invention, the computer system 180 can be programmed with a language translation program for translating text from one language to another language. For example, upon admission to the hospital, the patient can specify a desired or native language. Thus, text typed by a patient using the PCC 100 can be translated from the patient's specified language into English, and then be provided to the destination node. The English language response from a caregiver or visitor can, in turn, be translated to the patient's specified language.

Figure 2A:
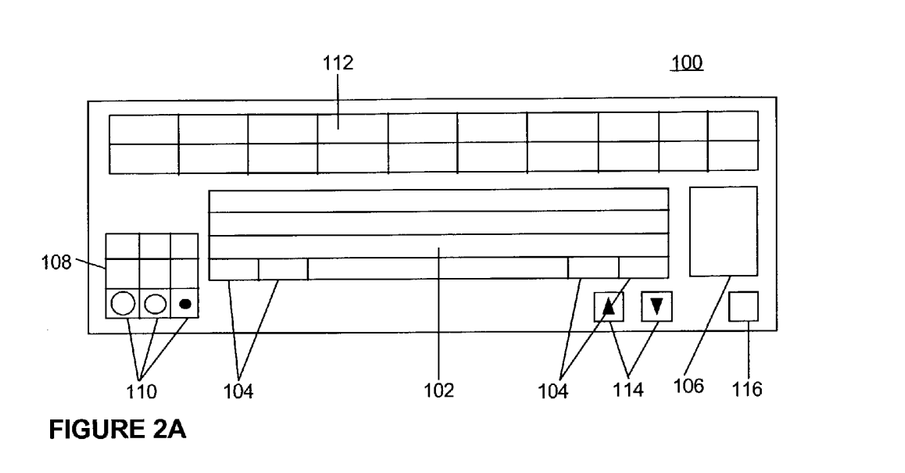
FIG. 2A is a schematic diagram illustrating an exemplary patient communication center in accordance with the inventive arrangements disclosed herein.

FIG. 2A is a schematic diagram illustrating an exemplary PCC 100 in accordance with the inventive arrangements of FIG. 1. As shown in FIG. 2A, the PCC 100 can include a combination of different alphanumeric keys and keys labeled with appropriate icons corresponding to particular pre-programmed patient needs or requests. The pre-programmed patient needs can be specified on a per patient basis thereby allowing each patient to specify one or more custom messages such as "please contact my son at 123-4567", or "please call my wife at "123-4567". In one embodiment, the pre-programmed messages can be programmed by the patient. Still, a system administrator can program the messages when the patient checks into the care-giving facility or at any time during the patient's stay. Regardless of how the messages are programmed, the PCC 100 can include icon labeled buttons having preprogrammed default messages as well as patient specific messages.

The PCC 100 can include a standard alphanumeric QWERTY keyboard portion 102 and a separate numeric portion 106. Using the keyboard portion 102 and the numeric portion 106, the patient can type any of a variety of messages or enter different selections. One or more destination buttons 104 can be provided. The destination buttons can be configured to route a particular message, whether typed or pre-programmed, to a particular destination. One destination button 104 can be provided for each location capable of communicating with the patient room 120. For example, a nutrition center button can route messages to the nutrition center and a visitor center button can route messages to the visitor center. Accordingly, responsive to activation of a destination button, a message can be routed to the computer system corresponding to the activated destination button 104. Despite the inclusion of one or more destination buttons, the PCC 100 can be configured to route messages to the nurse station by default.

The PCC 100 further can include a series of emergency buttons 108. Each of the buttons can correspond to a particular pre-programmed emergency. Still, as mentioned, particular emergency buttons can be programmed on a per patient basis. Accordingly, some of the buttons can be patient and/or condition specific. Urgency buttons 110 can be used to indicate the urgency of any non-emergency requests. For example, as shown, larger circles can indicate more urgent circumstances. Still, other visual identifiers can be used such as colors, symbols, icons, pictures, and the like. Buttons 114 can be speaker volume buttons for increasing or decreasing the audio volume. The audio volume, for example from the video monitor or an intercom, can be increased or decreased responsive to operation of the appropriate button. Button 116 can be a cancel call button allowing the patient to cancel a previous message or a request for a service. Buttons 112 can be additional pre-programmed or patient specific function buttons which can be labeled with an icon corresponding to the function of each button.

A list of potential function buttons has been included in Appendix A. Still, it should be appreciated that the list is for purposes of illustration only. Accordingly, the invention is not so limited to the particular functions listed or the particular physical layout of the buttons or keys of the PCC 100. For example, in one embodiment for use with children, the PCC 100 can include only large buttons having descriptive icons. In that case, an additional button can be included for requesting the child's parents. Depending upon the age of the patient to be using the PCC 100, the QWERTY keyboard portion need not be included.

According to one aspect of the present invention, the PCC 100 can have a default setting, which can be enabled or disabled, which monitors for activation of too many, or more than a predetermined number of icons or buttons at one time. The PCC 100 further can monitor for nonsensical button combinations as may be defined within a system profile. If such a condition is detected, the PCC 100 can override the various activated buttons and/or icons and transmit an emergency signal indicating that the patient may be experiencing a health emergency or may not be coherent. A similar functionality can be included wherein text messages are analyzed for spelling and or grammatical structure. If such a message includes more than a predetermined number of errors, the PCC 100 can send an emergency signal. The emergency functions described herein, however, also can be performed by a central server or computer system.

When possible, the icons on the PCC 100 keys can be commonly recognizable icons or other icons from the public domain to ensure that patients can intuitively operate the PCC 100. Regardless, the invention is not limited to any particular set of icons. Rather, humorous icons, different symbols, pictures, colors, and/or alphanumeric identifiers can be used. Preferably, the icon can provide the patient with an intuitive indication of the function of the button or key.

Each of the keys also can include a raised portion such as a brail letter, number, or symbol indicating the function or description of the button.

Patients can be provided with audible and visual feedback that a button has been activated. Responsive to activation of a button, an audible sound can be triggered. For example, if the "nurse" button is activated, a click can be generated or an audio prompt saying "nurse" can be generated, for example from a recording or using text-to-speech technology. The audible signals provide notification to the patient that the correct icon has been activated. Visual notification can be provided by placing the icon or text corresponding to the activated button on the video monitor. The icon or text can remain on the video monitor until the particular patient need has been met. At that time, or when disabled by a care-giver, the icon can be removed from the patient's video display.

In one embodiment of the invention, responsive to a first activation of a button, an audio prompt identifying the activated button can be played. Upon a second consecutive activation, after the patient has verified that the correct button has been selected, the function corresponding to the button can be activated, for example ringing the nurse station. Upon the second activation, the visual identifier can be placed on the patient's video display informing the patient that his or her message has been sent.

The PCC 100 can be encased within a strong, lightweight, and waterproof housing. An optional cover that can be wiped clean and sanitized can be included. For example, such a cover can be a disposable clear plastic protective cover having an elastic band holding the cover on the PCC 100. The PCC 100 can be attached or clipped to several types of holders, depending on the patient's needs or medical condition. For instance, if the patient has limited mobility, the PCC 100 can be attached to a freestanding arm extending over the patient's bed. The freestanding arm can be easily pushed out of the way allowing care-giver staff to perform routine or emergency procedures. The arm can be positioned so that the patient can easily reach the icons, even while in hand restraints. For example, the arm can operate similar to a typical patient table in that the arm can include a base unit on wheels which allows the base to be moved under the bed. The arm can be positioned to effectively raise or lower the PCC 100 as well as adjust the viewing angle of the PCC 100 to accommodate the patient's position. When the patient acquires greater mobility, the PCC 100 can be attached to the hospital table, clipped to the bed rail, or positioned in the patient's lap.

Figure 2B:
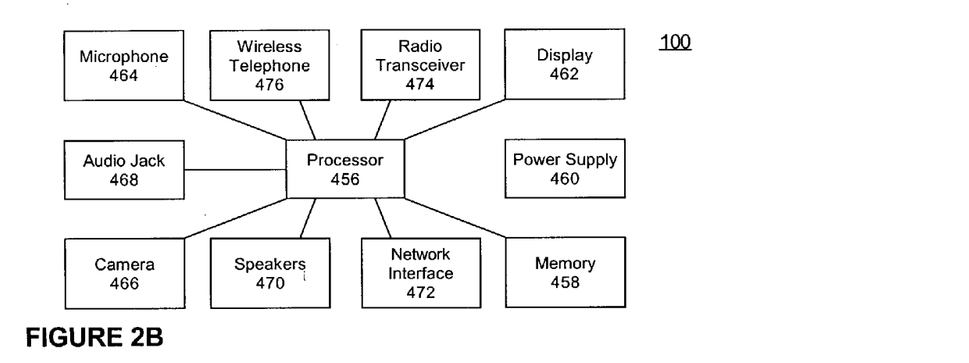
FIG. 2B is a schematic diagram illustrating another embodiment of the patient communication center in accordance with the inventive arrangements disclosed herein.

FIG. 2B is a schematic diagram illustrating another embodiment of the PCC 100 in accordance with the inventive arrangements disclosed herein. According to this embodiment, the PCC 100 can function as a standalone unit. For example, in such an embodiment, the PCC 100 can include a processor 456 and memory 458 such as random access memory, read-only memory, and/or another type of fixed storage. The processor 456 can include and execute a speech recognition engine and a text-to-speech engine. Other information such as programmed messages or software based systems as previously discussed can be stored locally within the PCC 100 as well. The PCC 100 further can include a power supply 460, for supplying power to the various components of the PCC 100 as may be required. The power supply 460 can be a conventional alternating current power supply which acquires electricity from a wall outlet, or can be a self-contained power supply, for example a rechargeable power supply.

As previously noted, the PCC 100 can include a display 462, whether suitable for displaying text, images, and/or motion video. The display can be a small liquid crystal display or another portable display which can be readily incorporated into the PCC 100. The PCC 100 also can include a microphone 464, a camera 466, one or more audio jacks 468 such as headphone outputs, and speakers 470. The PCC 100 can be configured with a suitable network interface 472 to communicate with other components or stations within a care giving facility. The network interface 472 can be implemented as a wired interface or as a wireless interface.

Notably, the PCC 100 can include a radio transceiver 474 and/or a wireless telephone 476. Accordingly, users can initiate communications to locations external to the network through which the PCC 100 communicates with other stations. Notably, in addition to conventional voice communications, the PCC 100 can be programmed to dial numbers or contact other parties via the wireless telephone 476 or radio transceiver 474 and play programmed messages once a connection has been established, for example, using text-to-speech technology or recorded messages. For example, the PCC 100 can be configured to dial "911" service responsive to activation of one or more keys.

Though the present invention is not limited to one particular type of configuration or implementation, such a configuration can be useful in the case where the PCC 100 is implemented as a portable and self-contained unit. For example, the PCC 100 can be used in an automobile or other situation wherein the PCC 100 is to function as a standalone unit. This would allow the user to send and receive messages, whether programmed, original, text, audio and/or video messages, to and from various locations.

The aforementioned components can be interconnected via suitable interface circuitry. For example, data, including audio and video can be routed among the various components using a suitable communications bus or other circuitry. Power connections (not shown) can be distributed from the power supply to the components of the PCC 100 as well.

Figure 3:
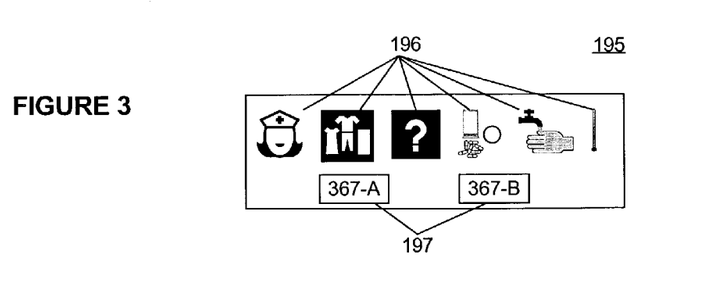
FIG. 3 is a schematic diagram illustrating one embodiment of a patient door display in accordance with the inventive arrangements disclosed herein.

FIG. 3 is a schematic diagram illustrating an exemplary embodiment of the patient door display. The icons 196 included in the patient door display 195 can correspond to one or more of the icons of the PCC buttons. Accordingly, upon activation of an icon, the corresponding icon of the patient door display 195 can be illuminated. The patient door display 195 can provide personnel outside of the patient room with a visual indication of the patient's particular need. The patient door display 195 functions separate from, and in addition to, any messages provided to the terminal located at the nurse station. The illuminated icon provides an indication, not only that a patient has a particular need, but also that the need has not been met. Once the patient need has been addressed, the illuminated icon can be turned off by a member of the care-giver staff.

It should be appreciated that each icon of the PCC 100 need not be included in the patient door display 195. For example, different icons such as emergency icons or non-emergency icons can be shown depending upon the patient and the patient's affliction. In one embodiment, the patient door display 195 can be a video display such that any of the PCC button icons can be displayed or removed. Alternatively, the patient door display can be a mechanical illuminated sign wherein different slip-in icon frames can be inserted to match the needs of a particular facility, patient, or illness. A two-bed room can include a room number indicator 197. This can notify care-giver staff which patient within a room has initiated a request.

In operation, and referring to FIGS. 1-3, when a patient first checks into a care-taking facility, the patient can provide pertinent information which can be entered into a data store such as a relational database or other patient management system which can be interfaced with the invention disclosed herein. For example, the patient can specify a native or preferred language, preferred foods, any allergies to foods or medication, as well as other pertinent information regarding designated visitors, form of payment, and the like.

Once in the patient room, the patient can operate the PCC to type messages or activate buttons having pre-programmed messages. In one mode of operation, the messages can be displayed upon the patient's video display to communicate with visitors or care-givers within the patient's room. In another mode of operation, messages can be routed to the nurse station or any other designated target location for which a corresponding button has been provided on the PCC. Correspondingly, each target location can respond to the patient. Sent and/or received messages, graphics, and text can be displayed upon the patient's video display. Because the video display can display a picture, a television program, a movie, or some other form of entertainment, any text and/or graphics generated by the present invention, whether from the PCC or another station, can be overlaid upon the video display.

If the patient activates a nurse call button, a corresponding visual indicator such as an icon can be displayed at the nurse station. The nurse can depress a button on the nurse keyboard which would give feedback in the patient's room indicating that the message was received. This could be a double beep tone or an audible message sent back saying "nurse on the way", "clean-up on the way", "food on the way", etc., depending on which icon was activated. Alternatively, a general response can be used which can say "Your message was received at the nurse station and someone is on the way now." Notably, if the patient specified a language other than English as the default language, the message can be translated to the desired language. The message can be provided as text on the patient's video display or can be played aloud, i.e. as a recorded message or using text-to-speech. Still, nurses can communicate with the patient by typing messages which can be displayed upon the patient's video display, or verbally through a patient room speaker. Depending upon whether the patient can respond verbally, the patient can provide a text response or a voice response. If a single video display is used to service several patients within a single room, the monitor can indicate which patient a displayed message or visual identifier is intended.

Figure 4:
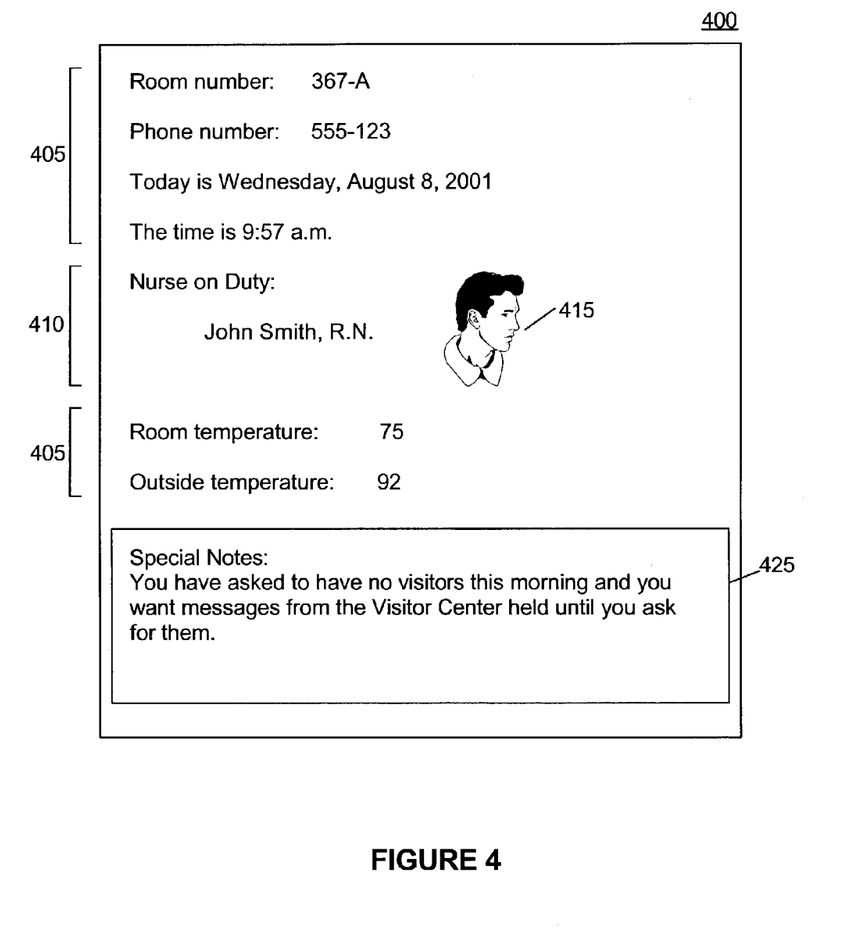
FIG. 4 is an illustration of a graphical user interface (GUI) which can be used with the inventive arrangements disclosed herein.

FIG. 4 is an illustration of an exemplary graphical user interface (GUI) 400 of the patient's video display in accordance with the inventive arrangements disclosed herein. As shown in FIG. 4, a variety of information can be displayed upon the patient video display. The display can provide several items of current information 405 including, but not limited to, the room number, the patient's room telephone number, the date, the time, as well as the temperature within the room and the outside temperature. On duty staff information 410 can provide the name of any attending nurse, physician, or other personnel. A picture 415 of each listed person can be included. Notably, the picture 415 provides an added measure of security for patients as well as staff. Unauthorized persons attempting to gain access to a patient or a care-taking facility can be identified more easily by patients and staff alike. This can be particularly useful with regard to patients who may require an added sense of security or safety such as battered wives/husbands or victims of other violent crimes or traumatic events.

An information box 425 can be included for listing any special notes such as dietary requirements, allergies, standing requests, or other information of note. GUI 400 can be, for example, a default screen which can be displayed when the patient activates the display or video monitor. Alternatively, GUI 400 can be displayed upon activation of the PCC. For example, responsive to activation of one or more of the PCC buttons, the PCC can generate a signal, either through the network or wirelessly, i.e. using radio frequency or infrared technology, to activate the video display. Different backgrounds also can be displayed within GUI 400. For example, various scenic views can be selected by the patient as background "wallpaper" for the video display. In one embodiment of the present invention, patients can provide digitized pictures which can be used as wallpaper for the video display.

Figure 5:
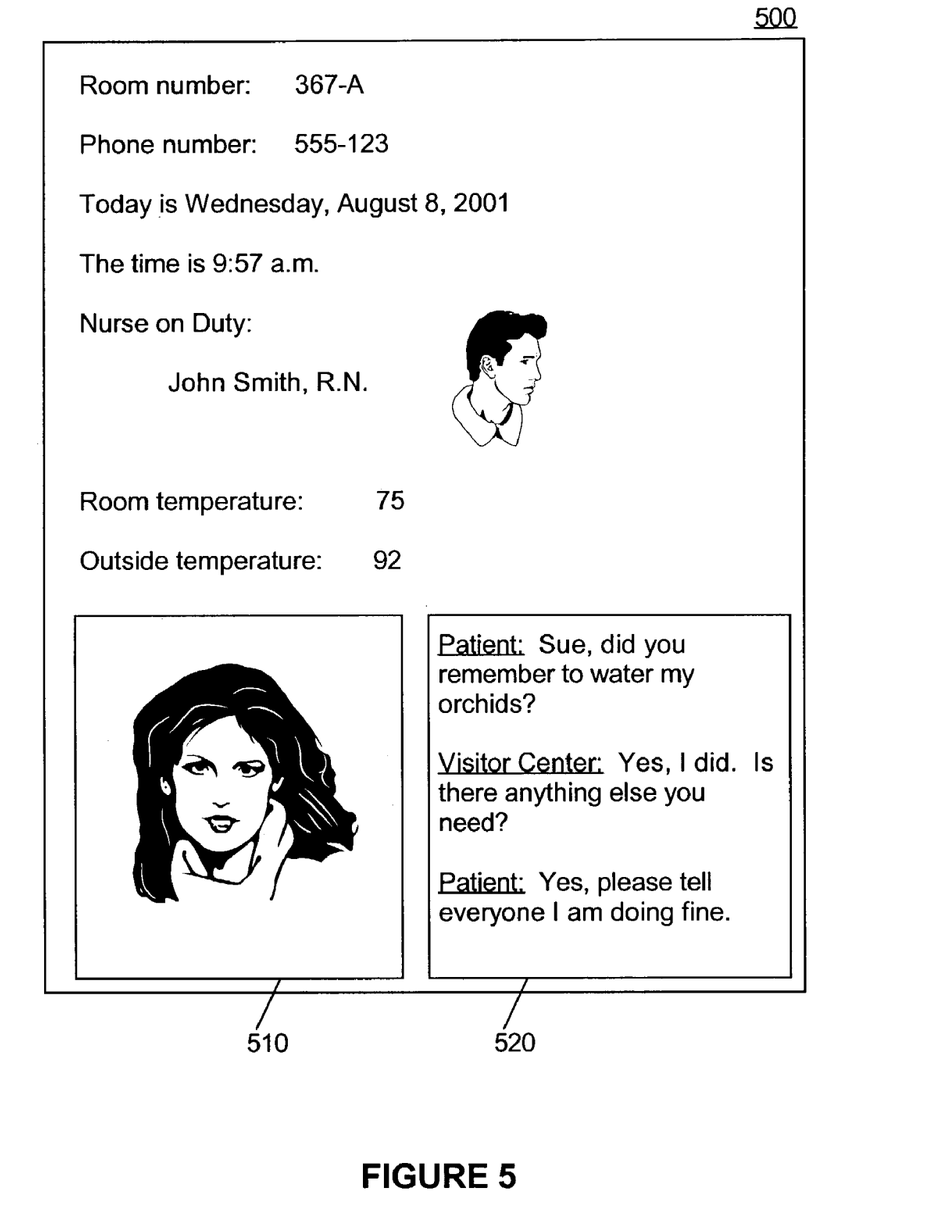
FIG. 5 is another illustration of a GUI which can be used with the inventive arrangements disclosed herein.

FIG. 5 is another illustration of an exemplary GUI 500. GUI 500 depicts the visitor center feature of the present invention. As shown, much of the information presented from GUI 400 also can be displayed within GUI 500. GUI 500, however, can include a window 510 containing a live video feed from the visitor center. While audio can be exchanged between the visitor center and the patient room, in this embodiment of the invention, a chat window 520 has been included. Using the chat function, a patient, who may not wish to be seen or heard, can interact with a visitor. As shown, the patient can view a live image of the visitor and correspond through text messages. In one embodiment of the invention, the text messages can be generated by a speech recognition engine rather than by manually typing the text. GUI 500 also can be used to playback pre-recorded video and audio messages from visitors.

Figure 6:
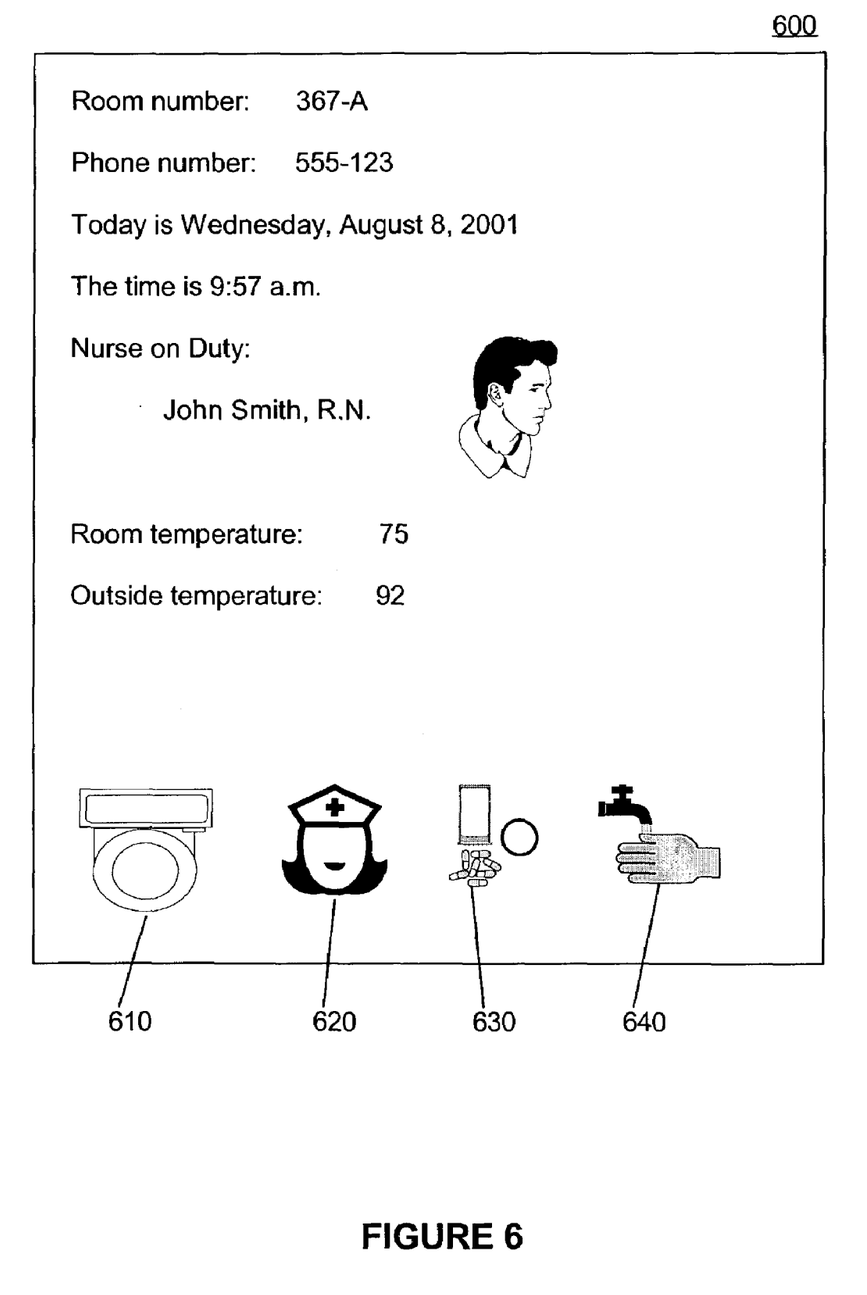
FIG. 6 is another illustration of a GUI which can be used with the inventive arrangements disclosed herein.

FIG. 6 is another illustration of an exemplary GUI 600 which can be provided to the patient's video display. As shown in FIG. 6, icons 610-640 have been illuminated or activated. In this embodiment of the invention, as the user activates a particular button on the PCC, the corresponding icon can appear on the patient's video display confirming that the patient has activated the proper button. Accordingly, the patient can either leave the button activated as indicated by the icons 610-640, or cancel one or more of the requests. In this case, the patient has activated a button requesting assistance in using the bathroom as indicated by icon 610. Icon 620 can indicate that the patient has requested the nurse. Icon 630 can indicate that the patient requires medication. Icon 640 can indicate that the patient requires assistance in washing. As mentioned, the icons also can be illuminated on the patient's door display, which can be located inside or outside of the patient's room. In any case, the invention is not limited to the particular icons used. Rather, any suitable color, symbol, picture, or alphanumeric character can be used as an indication of a particular service or request.

Figure 7:
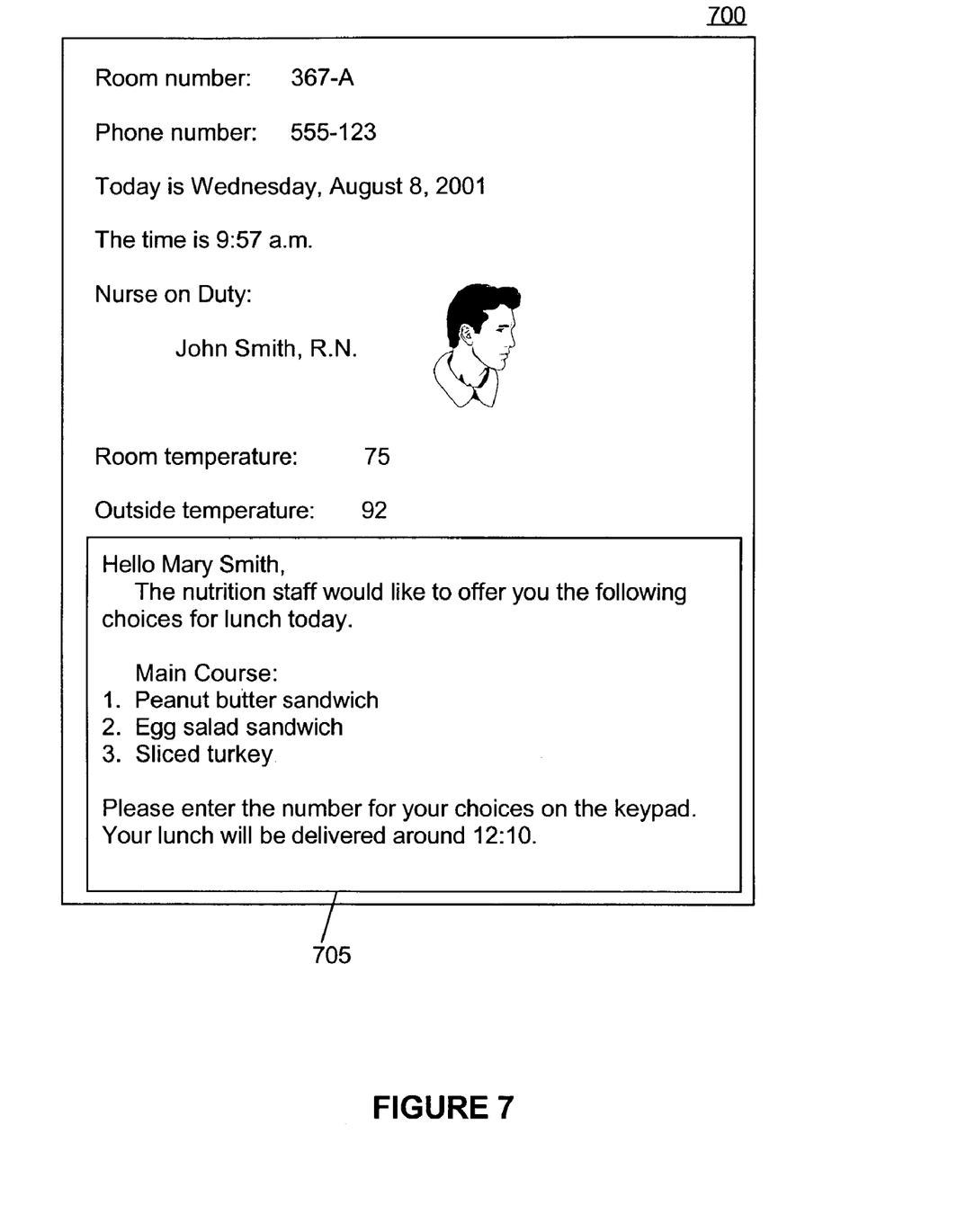
FIG. 7 is another illustration of a GUI which can be used with the inventive arrangements disclosed herein.

FIG. 7 is another illustration of an exemplary GUI 700 depicting an interaction between the nutrition center and the patient. As shown in FIG. 7, window 725 includes a message from the nutrition center asking the patient to choose a main course for lunch. The patient can select a main course by pressing the number corresponding to the desired selection. As mentioned, the selections offered to the patient can be filtered, and thereby individualized, in accordance with the information provided by the patient during check in. It should be appreciated that during check in, the patient can specify not only foods to which the patient is allergic, but also preferred, favorite, or disliked foods. Accordingly, any foods that the patient has indicated that cause allergic reactions, or which the patient dislikes can be removed from the menu selections presented in window 705.

Figure 8:
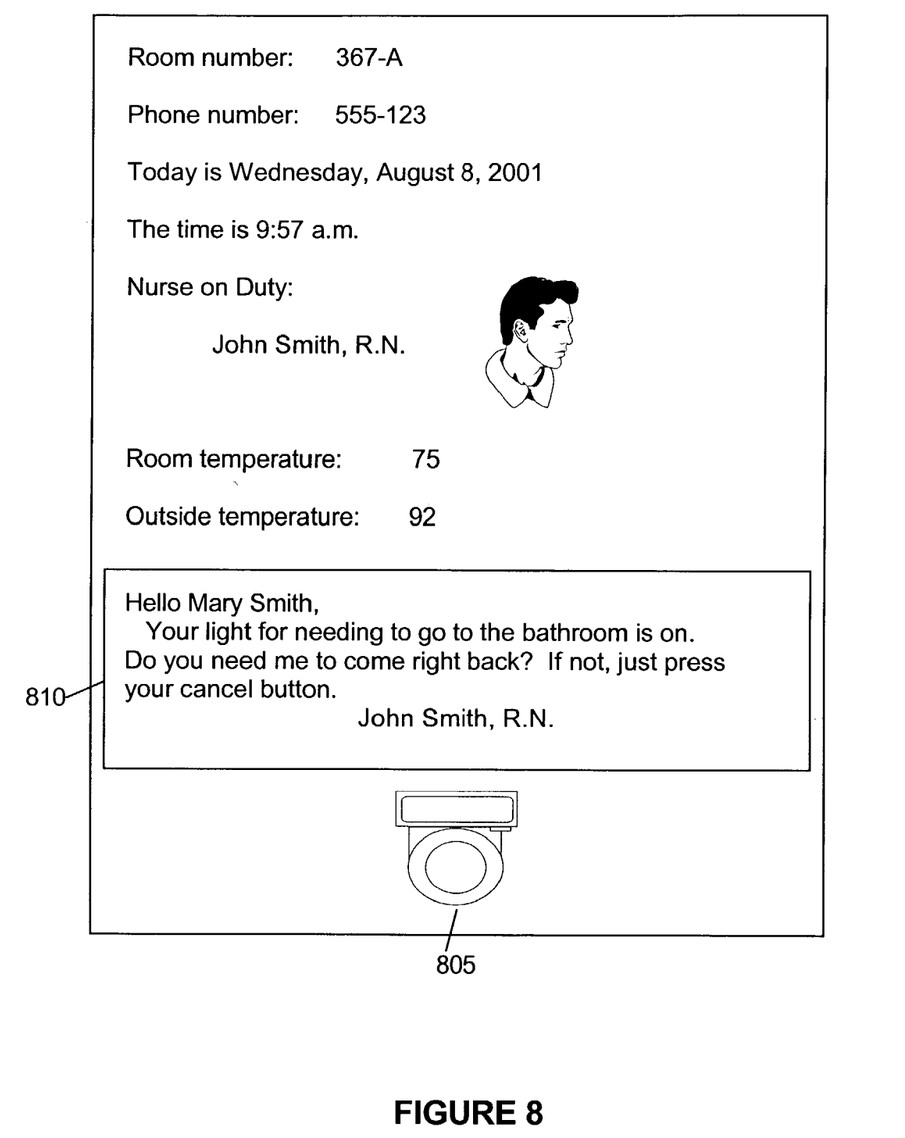
FIG. 8 is another illustration of a GUI which can be used with the inventive arrangements disclosed herein.

FIG. 8 is yet another illustration of an exemplary GUI 800 depicting the situation where a care-giver has previously responded to a patient request and either the bathroom icon 805 has been reactivated or was not turned off. Accordingly, in window 810, the on duty nurse has sent a text message to the patient asking whether the patient still requires assistance. A tone and/or a light, for example originating from the PCC or from another apparatus within the room, can notify the patient that a message is waiting on the patient's monitor.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

APPENDIX A

Fire
Nurse—help
Nurse—question
Doctor—question
Doctor—help
Suction
Nausea—upset stomach
Water
I'm frightened/need to talk
I don't understand
Pain
Toilet
Adjust in bed
Clean-up spill
Want to see family member
Clergy
Food
Remove food
Bandage—change dressing
Wheelchair
Shower/bath
Clean hair/face
Shave
Change dressing
Cords are tangled
Light
Phone
Reading material
Visitors/no visitors
Cancel
Help—general panic mode

What is claimed is:

1. A healthcare communication system comprising:
a patient terminal comprising a keyboard unit having message keys for generating different ones of a plurality of programmed messages and alphanumeric keys for composing messages, wherein said patient terminal is communicatively linked to a patient terminal display for presenting said plurality of programmed messages and composed messages, each said message key having a surface portion and unique identifying indicia disposed on the surface portion and corresponding to a particular programmed patient message that is transmitted over the communication system after a patient selects said message key, the identifying indicia symbolically indicating a type of the particular programmed message;
a memory communicatively linked to the patient terminal for storing the programmed messages, wherein the plurality of programmed messages include at least one patient-specific message composed by a patient or other person using the keyboard unit, wherein the at least patient-specific message is associated with one of the message keys, defining an activation key, to enable the patient to send the message by pressing the activation key, and wherein the at least one patient-specific message can be sent by the patient to a patient-directed destination by the patient pressing one or more other message keys, defining destination keys;
a visitor center remotely located from and communicatively linked to the patient terminal, wherein the system is configured to convey visitor messages from the patient to a visitor and to convey visitor messages to the patient from the visitor, wherein the patient can store a visitor message in the memory and retrieve the stored visitor message from the memory at a latter time, and wherein the patient can direct the system to automatically store visitor messages from a particular class of visitors by identifying the particular class;
a nurse station remotely located from and communicatively linked to the patient terminal for receiving assistance messages from the patient, wherein the system dates and time-stamps each assistance message for performing quality control monitoring; and
a patient-door display communicatively linked to the patient terminal for displaying a care-giver notice when an associated message key is pressed by the patient.

2. The system of claim 1, wherein said patient terminal display is configured to display an image of at least one care-giver assigned to a user of said patient terminal.

3. The system of claim 1, wherein said patient terminal display is disposed within said patient terminal.

4. The system of claim 1, said patient terminal further comprising:
a wireless communication component for transmitting said messages to at least one receiving station.

5. The system of claim 1, wherein said programmed messages are selected from the group consisting of text messages, audio messages, visual messages, and audiovisual messages.

6. The system of claim 1, wherein a first activation of one of said message keys causes a notification to be provided indicating the identity of said activated message key, and a second activation of said message key causes a message associated with said activated message key to be sent.

7. The system of claim 1, wherein said visitor station communicatively linked to said patient terminal comprises an audiovisual component for generating audiovisual information of at least one visitor and playing received audiovisual information.

8. The system of claim 7, said patient terminal further comprising:
an audiovisual component for generating audiovisual information and for playing said audiovisual information from said visitor station, wherein the visual information of said audiovisual information is presented through said patient terminal display.

9. The system of claim 7, wherein the visual information of said audiovisual information specifies an image of a visitor using said visitor station, and wherein said patient terminal display is configured to display said image of said visitor.

10. The system of claim 8, wherein the visual information of said audiovisual information generated by said patient terminal specifies an image of a user of said patient terminal, and wherein said visitor station is configured to display said image of said user.

11. The system of claim 8, further comprising:
a data store for recording said audiovisual data for delayed playback through said visitor station or said patient terminal.

12. The system of claim 1, further comprising:
a second display having at least one visual status indicator corresponding to said plurality of programmed messages, wherein one of said visual status indicators is illuminated responsive to a user selection of a corresponding one of said programmed messages.

13. The system of claim 1, further comprising:
a nutrition station configured to transmit messages specifying at least one food item choice to said patient terminal for presentation upon said patient terminal display and to receive messages from said patient terminal specifying selected ones of said food item choices indicating food items to be prepared and delivered.

14. The system of claim 13, wherein said data store further comprises patient specific dietary information, said nutrition station configured to present only food item choices according to said patient specific dietary information.

15. The system of claim 1, wherein the nursing station comprises a keyboard and display configured to receive said messages and to transmit messages to said patient terminal.

16. The system of claim 15, wherein said display of said nursing station displays a listing of one or more authorized visitors, unauthorized visitors, or both authorized and unauthorized visitors for a patient.

17. The system of claim 16, wherein said display of said nursing station further displays visual images of said authorized and unauthorized visitors.

18. The system of claim 11, further comprising:
a message logger for storing, within said data store, message transmission information and message response information for messages generated by said patient terminal, a nutrition station, and said nursing station.

19. The system of claim 18, further comprising:
an administrative station configured to generate performance metric reports according to said message transmission information and said message response information.

20. The system of claim 1, further comprising:
a speech recognition system configured to convert an audio message to text.

21. The system of claim 1, further comprising:
a translation system configured to translate text specified in said messages from a first language to a second language.

22. The system of claim 21, further comprising:
a speech recognition system configured to convert an audio message to text and provide said speech recognized text to said translation system.

23. The system of claim 1, wherein the the identifying indicia is a pictorial symbol representative of the programmed patient message.

* * * * *